US009968607B2

(12) United States Patent
Parthasaradhi Reddy et al.

(10) Patent No.: US 9,968,607 B2
(45) Date of Patent: May 15, 2018

(54) PHARMACEUTICAL COMPOSITIONS OF RALTEGRAVIR, METHODS OF PREPARATION AND METHODS OF USE THEROF

(75) Inventors: Bandi Parthasaradhi Reddy, Hyderabad (IN); Podili Khadgapathi, Hyderabad (IN); Goli Kamalakar Reddy, Hyderabad (IN)

(73) Assignee: HETERO RESEARCH FOUNDATION, Hyderabad, Andhra Pradesh (IN)

( * ) Notice: Subject to any disclaimer, the term of this patent is extended or adjusted under 35 U.S.C. 154(b) by 0 days. days.

(21) Appl. No.: 13/446,114

(22) Filed: Apr. 13, 2012

(65) Prior Publication Data
US 2012/0270888 A1 Oct. 25, 2012

(30) Foreign Application Priority Data

Apr. 25, 2011 (IN) .......................... 1414/CHE/2011

(51) Int. Cl.
*A61K 31/513* (2006.01)
*A61K 9/20* (2006.01)

(52) U.S. Cl.
CPC .......... *A61K 31/513* (2013.01); *A61K 9/2027* (2013.01); *A61K 9/2031* (2013.01)

(58) Field of Classification Search
None
See application file for complete search history.

(56) References Cited

U.S. PATENT DOCUMENTS

| 5,273,758 | A | * | 12/1993 | Royce | .................. | A61K 9/2031 424/464 |
| 7,169,780 | B2 | | 1/2007 | Crescenzi et al. | | |
| 7,754,731 | B2 | | 7/2010 | Belyk et al. | | |
| 2006/0177506 | A1 | | 8/2006 | Yanai et al. | | |
| 2010/0178339 | A1 | * | 7/2010 | Koo et al. | .................. | 424/465 |
| 2012/0328568 | A1 | * | 12/2012 | Cummings et al. | ......... | 424/85.7 |

FOREIGN PATENT DOCUMENTS

| WO | 2006060681 | A2 | 6/2006 |
| WO | 2006060711 | A2 | 6/2006 |
| WO | 2010140156 | A2 | 12/2010 |
| WO | WO 2010140156 | A2 * | 12/2010 |
| WO | WO 2010143207 | A1 * | 12/2010 |
| WO | 2012147101 | A2 | 11/2012 |

OTHER PUBLICATIONS

Sigma-Aldrich, Poly(ethylene glycol) and Poly(ethylene oxide), http://www.sigmaaldrich.com/materials-science/material-science-products.html?TablePage=20204110, uploaded Jan. 27, 2014.*
Shah, Polyethylene Glycol as a Binder for Tablets, Journal of Pharmaceutical Sciences, 66(11), 1977, pp. 1551-1552.*
RN 25322-68-3, Chemical Abstracts, Entered STN: 1984, pp. 1-2.*
Maggi, Dissolution behaviour of hydrophilic matrix tablets containing two different polyethylene oxides (PEOs) for the controlled release of a water-soluble drug. Dimensionality study, Biomaterials, 2002, 23, pp. 1113-1119.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
International Search Report for International Application No. PCT/IN2012/000283, International Application Filing Date: Apr. 19, 2012; dated Nov. 28, 202, 4 pages.
U.S. Appl. No. 14/056,254, filed Oct. 17, 2013; Non-final Office Action dated May 8, 2014; 20 pages.
Polyethylene Glycol in "Handbook of Pharmaceutical Excipients"; fourth edition; edited by Raymond C. Rowe; Royal Pharmaceutical Society of Great Britain; London, UK; 2003; pp. 454-459.
Polyethylene Oxide in "Handbook of Pharmaceutical Excipients"; fourth edition; edited by Raymond C. Rowe; Royal Pharmaceutical Society of Great Britain; London, UK; 2003; pp. 460-461.
Hicks, et al.; "Raltegravir: The First HIV Type 1 Integrase Inhibitor"; Reviews of Anti-Infective Agents; CID; 48; pp. 931-939; (2009).
Maggi et al.; dissolution Behaviour of Hydrophilic Matrix Tablets Containing Two Different Polyethylene Oxides (PEOs) for the Controlled Release of a Water-Soluble Drug. Dimensionality Study; Biomaterials; 23; pp. 1113-1119; (2002).

* cited by examiner

*Primary Examiner* — Kathrien A Cruz
*Assistant Examiner* — Andrew Lee
(74) *Attorney, Agent, or Firm* — Cantor Colburn LLP

(57) ABSTRACT

Disclosed are pharmaceutical compositions comprising HIV integrase strand transfer inhibitor. More particularly, oral pharmaceutical compositions of raltegravir or its pharmaceutically acceptable salts and process for preparing and use of the same are disclosed.

13 Claims, No Drawings

PHARMACEUTICAL COMPOSITIONS OF RALTEGRAVIR, METHODS OF PREPARATION AND METHODS OF USE THEROF

CROSS-REFERENCE TO RELATED APPLICATION

This application claims priority to India Patent Application No. 1414/CHE/2011, filed Apr. 25, 2011, the contents of all applications being incorporated by reference herein in their entirety.

FIELD

Disclosed herein are pharmaceutical compositions comprising HIV integrase strand transfer inhibitor. More particularly, oral pharmaceutical compositions of raltegravir or its pharmaceutically acceptable salts and process for preparing and use of the same are disclosed.

BACKGROUND

Raltegravir and its pharmaceutically acceptable salt or solvate thereof were disclosed in U.S. Pat. No. 7,169,780. Chemically raltegravir potassium is N-[(4-Fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide monopotassium salt having the following structural formula:

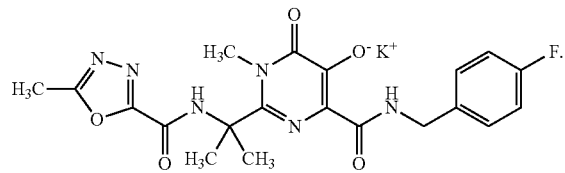 [SMILES: Cc1nnc(C(=O)NC(C)(C)c2nc(C(=O)NCc3ccc(F)cc3)c([O-])c(=O)n2C)o1 ; [K+]]

Raltegravir potassium, a human immunodeficiency virus integrase strand transfer inhibitor, is indicated in combination with other antiretroviral agents for the treatment of HIV-1 infection.

Raltegravir is commercially available as a prescription medicine from Merck, under the trade name ISENTRESS® (Raltegravir Potassium) for the treatment of HIV infections. Approved in 2007 by the U.S. Food and Drug Administration, ISENTRESS® is currently available in the form of 400 milligram (mg) oral tablets.

U.S. Pat. No. 7,754,731 assigned to Merck claims anhydrous crystalline potassium salt of raltegravir.

WO2006060681 assigned to Merck claims compositions of raltegravir potassium comprising an antinucleating agent selected from hydroxyalkylcellulose, alkylcellulose, polyvinylpyrrolidone and polyacrylic acid.

WO2006060711 assigned to Merck claims oral formulations of raltegravir potassium comprising poloxamer as a solubilizing agent, and high viscosity hydroxypropylmethylcellulose and glyceryl behenate as gelling agent.

WO2010140156 assigned to Hetero Research Foundation discloses amorphous raltegravir potassium, and crystalline Form H1 of raltegravir potassium.

There remains a need to develop formulations of raltegravir using conventional techniques and equipment which is easy to manufacture.

SUMMARY OF INVENTION

It has been found that compositions of raltegravir comprising non-gelling polymers are comparable with the marketed raltegravir potassium formulation.

In one embodiment, a pharmaceutical composition comprises as active ingredient raltegravir or its pharmaceutically acceptable salt thereof, non-gelling polymer and one or more pharmaceutically acceptable excipients.

In another embodiment, a pharmaceutical composition comprises raltegravir, non-gelling polymer selected from polymethacrylates and/or polyethylene oxide, and one or more pharmaceutically acceptable excipients, characterized in that said composition is free of anti-nucleating agent.

In another embodiment, a process for preparing a pharmaceutical composition comprising raltegravir, non-gelling polymer and at least one pharmaceutically acceptable excipient, comprises using wet granulation, dry granulation, spray granulation, direct compression or extrusion-spheronization, wherein the composition is free of anti-nucleating agent and solubilizing agent.

In one aspect, a wet granulation process for preparing compressed tablet of raltegravir, comprising non-gelling polymer, comprises: (i) dry mixing raltegravir with one or more excipients, (ii) wet granulating the dry mix of step (i) using binder solution to form granules followed by drying, (iii) lubricating the dried granules with all or none or remaining portion of the excipients and compressing into tablets.

In a further aspect, the process for preparing a compressed tablet of raltegravir, comprising non-gelling polymer, by dry granulation comprises: (i) sifting and blending the raltegravir with one or more excipients, (ii) compressing the blended mixture of step (i) to form slugs and then sizing the resulting slugs to form granules; (iii) blending the granules with remaining portion of the excipients; and (iv) compressing the granules of step (iii) into tablets.

In yet another aspect, a tablet composition comprises raltegravir potassium, non-gelling polymer selected from polymethacrylates and/or polyethylene oxide and one more pharmaceutically acceptable excipients, characterized in that said composition is free of anti-nucleating agent and solubilizing agent.

DETAILED DESCRIPTION

By "salts" or "pharmaceutically acceptable salts", it is meant those salts and esters which are, within the scope of sound medical judgment, suitable for use in contact with the tissues of humans and lower animals without undue toxicity, irritation, and allergic response, commensurate with a reasonable benefit to risk ratio, and effective for their intended use.

"Free from" or "Free of" used here synonymously means that the ingredient is not intentionally added as a major ingredient during preparation of a composition; the composition can contain trace amounts of the ingredient, such as less than about 2%, or 1%, or 0.5%, by weight.

A pharmaceutical composition comprises raltegravir or its pharmaceutically acceptable salt thereof, non-gelling polymer and one or more pharmaceutically acceptable excipients.

The non-gelling polymer can be present in the composition in an amount of about 0.5 to about 20 percent weight/weight (% w/w), specifically about 1 to about 15% w/w, and yet more specifically about 3 to about 10% w/w based on the total weight of the composition.

The pharmaceutically acceptable excipient can be present in the composition in an amount of about 1 to about 50 percent % w/w, specifically about 15 to about 45% w/w, and yet more specifically about 30 to about 40% w/w based on the total weight of the composition.

A pharmaceutical composition comprises raltegravir, non-gelling polymer selected from polymethacrylates and/or polyethylene oxide and one more pharmaceutically acceptable excipients, characterized in that said composition is free of anti-nucleating agent.

"Anti-nucleating agent" means a water-soluble polymer. The term "water-soluble polymer" means any polymer which is freely soluble in water or which dissolves or solubilizes in water (e.g., in an amount of at least about 0.005 mg/ml). Exemplary water-soluble polymers include hydroxyalkylcelluloses, alkylcelluloses, polyvinylpyrrolidones, and polyacrylic acids "Non-gelling polymer" means a polymer that is insoluble and essentially un-swellable upon contact with an aqueous medium, specifically water. Non-gelling polymer specifically excludes water soluble (e.g., in an amount of at least about 0.005 mg/ml) and/or water swellable polymers such as hydroxyalkylcelluloses, alkylcelluloses, polyvinylpyrrolidones, and polyacrylic acids.

Suitable non-gelling polymethacrylates include by way of example and without limitation, poly (ethyl acrylate, methyl methacrylate, trimethylammonioethyl methacrylate chloride) polymer, poly (ethyl acrylate, methyl methacrylate) polymer, a methacrylic acid-methyl methacrylate co-polymer, a methacrylic acid-ethyl acrylate co-polymer, poly (methyl acrylate, methyl methacrylate, methacrylic acid) or combination thereof. The non-gelling polymers exclude polyacrylic acids such as carbomer polymers (Carbopol). Exemplary non-gelling polymers include Eudragit RL (poly (ethyl acrylate-co-methyl methacrylate-co-trimethylammonioethyl methacrylate chloride) 1:2:0.2), and Eudragit RS (poly(ethyl acrylate-co-methyl methacrylate-co-trimethylammonioethyl methacrylate chloride) 1:2:0.1), Eudragit NE 30 D (poly(ethyl acrylate-co-methyl methacrylate) 2:1), Eudragit L30 D-55 (poly(methacrylic acid-co-ethyl acrylate) 1:1), Eudragit FS 30D (poly(methyl acrylate-co-methyl methacrylate-co-methacrylic acid) 7:3:1), Eudragit L100 55 (poly(methacylic acid-co-ethyl acrylate) 1:1), Polyethylene oxide (Sentry Polyox) or combinations thereof. It is noted that polyethylene oxide is different from polyethylene glycol. Polyethylene oxide is a high molecular weight non ionic homopolymer of ethylene oxide and having the molecular formula $(CH_2CH_2O)_n$. In comparison, polyethylene glycol is a low molecular weight addition polymer of ethyleneoxide and water, and having the molecular formula is $H(OCH_2CH_2)_nOH$, where n represents the average number of oxyethylene groups.

The pharmaceutical compositions can be made into solid dosage forms such as tablets, capsules, Multiple Unit Pellet System (MUPS), granules, solid dispersions, pellets, beads, particles, mini-tablets, orally disintegrating tablets and the like.

Accordingly, in one embodiment, the pharmaceutical oral composition comprises raltegravir, non-gelling polymers and one or more excipients selected from diluents, binders, lubricants and/or glidants.

Suitable diluents include talc, lactose, sugar, starches, modified starches, mannitol, sorbitol, inorganic salts, cellulose derivatives (e.g. microcrystalline cellulose), calcium sulfate, xylitol, lactitol, starch, pregelatinized starch, kaolin, sucrose, mannitol, sorbitol, dextrates, dextrin, maltodextrin, dextrose, calcium carbonate, calcium sulfate, dibasic calcium phosphate, tribasic calcium phosphate, magnesium carbonate, magnesium oxide and the like and mixtures thereof.

The term "binders" as used herein is intended to mean substances used to cause adhesion of powder particles in tablet granulations. Suitable binders include, by way of example and without limitation, lactose, starches such as corn starch, potato starch, modified starches, sugars, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, sodium alginate, acacia, alginic acid, tragacanth, carboxymethylcellulose sodium, ethyl cellulose, gelatin, liquid glucose, povidone and pregelatinized starch, and the like or mixtures thereof.

The term "lubricant" as used herein is intended to mean substances used in tablet formulations to reduce friction during tablet compression. Suitable lubricants include, by way of example and without limitation, calcium stearate, magnesium stearate, sodium stearyl fumarate, zinc stearate, stearic acid, fumaric acid, palmitic acid, talc, carnauba wax, hydrogenated vegetable oils, mineral oil, polyethylene glycols and the like or combinations thereof.

The term "glidant" as used herein is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc and the like or combinations thereof.

The tablets may be coated with an aqueous or non aqueous solution or dispersion of film forming agents. Optionally, the film coat may be an aqueous moisture barrier. The coating solution mainly comprises of film forming polymers and one or more of plasticizers, opacifiers, surfactants, anti tacking agents, coloring agents and the like.

The coating can be applied by solubilizing or suspending the excipients in solvents such as isopropyl alcohol, water, acetone, ethanol, methylene chloride and the like or mixtures thereof.

Also provided herein is a process for preparing a pharmaceutical composition comprising raltegravir, non-gelling polymer and at least one pharmaceutically acceptable excipient, using wet granulation, dry granulation, spray granulation, direct compression, or extrusion-spheronization wherein the composition is free of anti-nucleating agent and solubilizing agent.

"Solubilizing agent" means an agent that acts to prevent or minimize precipitation of raltegravir in the gastrointestinal tract by maintaining it in a solubilized form for several hours following administration; solubilizing agents include poloxamers and fatty acid macrogolglycerides.

Direct compression process for preparing raltegravir tablets comprises the steps of: (i) dry mixing raltegravir with one or more excipients followed by blending, (ii) lubricating the blend obtained in step (i), and (iii) finally compressing the blend of step (ii) into tablets.

Dry granulation involves; (a) sifting and blending the raltegravir with one or more excipients (b) compressing the blended mixture of step (a) to form slugs and then sizing the resulting slugs to form granules; (c) blending the granules with all or none or remaining portion of the excipients; and (d) compressing the granules of step (c) in to tablets.

Alternatively, dry granulation involves; compacting raltegravir and other excipients in a roller compactor; and the compacts obtained were passed through ASTM Sieve #20 to obtain granules. The granules were lubricated and compressed into tablets on a rotary compression machine and the tablets were optionally coated with Opadry.

In one embodiment, a tablet composition comprising raltegravir, non-gelling polymer and one more pharmaceutically acceptable excipients, wherein the composition is free of anti-nucleating agent and solubilizing agent; wherein the tablet is prepared by either direct compression or dry granulation.

In another embodiment, the tablet composition of raltegravir comprising polyethylene oxide a non-gelling polymer and one more pharmaceutically acceptable excipients, is free of anti-nucleating agent and solubilizing agent.

Tablet composition comprising raltegravir, non-gelling polymethacrylates such as poly (ethyl acrylate, methyl methacrylate, trimethylammonioethyl methacrylate chloride) polymer, poly (ethyl acrylate, methyl methacrylate) polymer, a methacrylic acid-methyl methacrylate co-polymer, a methacrylic acid-ethyl acrylate co-polymer, poly (methyl acrylate, methyl methacrylate, methacrylic acid) or combination thereof and one more pharmaceutically acceptable excipients, wherein the composition is free of anti-nucleating agent and solubilizing agent.

Compositions of raltegravir comprising non-gelling polymers will improve the pharmacokinetic parameters by delaying the drug release in acidic pH and thereby delaying the $T_{max}$.

The term "raltegravir" as used herein includes raltegravir in the form of the free base, in the form of a pharmaceutically acceptable salt, amorphous raltegravir potassium, raltegravir potassium crystalline Form H1, crystalline raltegravir potassium monohydrate, crystalline raltegravir potassium dihydrate or any isomer, derivative, hydrate, solvate, or prodrug or combinations thereof.

In one embodiment, a method of treating a patient in need of raltegravir treatment comprises administering to a patient a pharmaceutical composition comprising raltegravir or a pharmaceutically acceptable salt thereof, a non-gelling polymer, and one or more pharmaceutically acceptable excipients.

The invention is further exemplified with following examples and is not intended to limit the scope of the inventions. Those skilled in the art can determine the composition for other dosage forms and substitute the equivalent excipients as described in this specification or with those known to the industry without undue experimentation.

EXAMPLES 1-4

Compositions of Raltegravir Tablets Prepared by Dry Granulation

| S. No | Ingredients | Example-1 Mg/tablet | Example-2 Mg/tablet | Example-3 Mg/tablet | Example-4 Mg/tablet |
|---|---|---|---|---|---|
| | Intragranular portion | | | | |
| 1 | Raltegravir potassium | 434.4 | 434.4 | 434.4 | 434.4 |
| 2 | Microcrystalline cellulose | 231.5 | 297.4 | 261.3 | 211.5 |
| 3 | Lactose monohydrate | 50 | 15 | 25 | 40 |
| 4 | Eudragit RL PO | 26.1 | — | — | — |
| 5 | Polyethylene oxide | 17.4 | 17.4 | 43.5 | 78.3 |
| 6 | Magnesium stearate | 7 | 7 | 7 | 7 |
| 7 | Sodium stearyl fumarate | 4 | 4 | 4 | 4 |
| | Extragranular portion | | | | |
| 8 | Microcrystalline cellulose | 93.6 | 86.1 | 86.1 | 86.1 |
| 9 | Magnesium stearate | 6 | 8.7 | 8.7 | 8.7 |
| | Core tablet weight | 870 | 870 | 870 | 870 |
| | Coating | | | | |
| 10 | Opadry II Pink | 21.75 | 21.75 | 21.75 | 21.75 |
| 11 | Purified water | q.s | q.s | q.s | q.s |
| | Total weight | 891.75 | 891.75 | 891.75 | 891.75 |

Brief manufacturing process:
i) Intragranular materials were sifted and blended together,
ii) the blended material of step no (i) was slugged/compacted and the resulted slugs/compacts were milled using multimill or cone mill,
iii) milled granules of step (ii) were sifted through #30 mesh completely,
iv) extra granular materials were sifted together through #40 mesh,
v) extra granular magnesium stearate was sifted through #60 mesh,
vi) materials of step (iii), (iv) and (v) were blended together and compressed into tablets,
vii) compressed tablets were optionally coated with Opadry II Pink.

EXAMPLES 5-8

Compositions of Raltegravir Tablets Prepared by Wet Granulation

| S. No | Ingredients | Example-5 Mg/tablet | Example-6 Mg/tablet | Example-7 Mg/tablet | Example-8 Mg/tablet |
|---|---|---|---|---|---|
| | Intragranular portion | | | | |
| 1 | Raltegravir potassium | 434.4 | 434.4 | 434.4 | 434.4 |
| 2 | Microcrystalline cellulose | 300 | 300 | 300 | 280 |
| 3 | Lactosemonohydrate | 25 | 25 | 25 | 25 |
| | Binder Solution | | | | |
| 4 | Eudragit RL PO | 8.7 | — | — | — |
| 5 | Eudragit NE 30 D | — | 9 | — | — |
| 6 | Eudragit FS 30 D | — | — | 9 | — |
| 7 | Eudragit L 100 55 | — | — | — | 10 |
| 8 | Isopropyl Alchohol | q.s | — | — | q.s |
| 9 | Acetone | q.s | — | — | q.s |
| 10 | Purified Water | — | q.s | q.s | — |
| | Extragranular portion | | | | |
| 11 | Microcrystalline cellulose | 93.2 | 92.9 | 92.9 | 111.9 |
| 12 | Magnesium stearate | 8.7 | 8.7 | 8.7 | 8.7 |
| | Core tablet weight | 870 | 870 | 870 | 870 |

-continued

| S. No | Ingredients | Example-5 Mg/tablet | Example-6 Mg/tablet | Example-7 Mg/tablet | Example-8 Mg/tablet |
|---|---|---|---|---|---|
| | Coating | | | | |
| 13 | Opadry II Pink | 21.75 | 21.75 | 21.75 | 21.75 |
| 14 | Purified water | q.s | q.s | q.s | q.s |
| | Total weight | 891.75 | 891.75 | 891.75 | 891.75 |

Brief manufacturing process:
viii) Intragranular materials were sifted and blended together,
ix) the blended material of step no (i) was granulated using binder solution and the resulted granules were dried and milled using multimill or cone mill,
x) milled granules of step (ii) were sifted through #20 mesh completely,
xi) extra granular materials were sifted together through #40 mesh,
xii) extra granular magnesium stearate was sifted through #60 mesh,
xiii) materials of step (iii), (iv) and (v) were blended together and compressed into tablets,
xiv) compressed tablets were optionally coated with Opadry II Pink.

EXAMPLE 9

Tablet Compositions of Raltegravir Prepared by Extrusion-spheronization Method:

| S. No | Ingredients | Mg/tablet |
|---|---|---|
| | Intragranular | |
| 1 | Raltegravir potassium | 434.40 |
| 2 | Microcrystalline cellulose | 254.30 |
| 3 | Lactose monohydrate | 25.00 |
| 4 | Eudragit RL PO | 8.70 |
| 5 | Purified water | q.s |
| 6 | Isopropyl Alchohol | q.s |
| | Extragranular | |
| 7 | Microcrystalline cellulose | 138.90 |
| 8 | Magnesium stearate | 8.70 |
| | Core tablet weight | 870.00 |
| 6 | Opadry pink | 21.75 |
| 7 | Purified water | q.s |
| | Total tablet weight | 891.75 |

Brief manufacturing process:
i) Intragranular materials were sifted and granulated with purified water using rapid mixer granulator,
ii) the wet granules of step no (i) was extruded and the resulted extrudes were spheronized using spherodizer to obtain spherical granules,
iii) spherical granules of step (ii) were dried completely,
iv) extra granular materials were sifted together through #40 mesh,
v) extra granular magnesium stearate was sifted through #60 mesh,
vi) materials of step (iii), (iv) and (v) were blended together and compressed into tablets,
vii) compressed tablets were optionally coated with Opadry II Pink.

EXAMPLE 10

Comparison of a Raltegravir Tablet Prepared with a Non-gelling Polymer Compared To a Raltegravir Tablet Prepared without a Non-gelling Polymer:

Raltegravir potassium is highly sensitive in acidic pH as it may get precipitated or degraded. It has been found that the use of a non-gelling polymer in a raltegravir formulation will not allow release, or slightly delays the active agent release, the formulation in the acidic pH range such as found in the stomach, thereby extending the formulation's $T_{max}$ and decreasing the $C_{max}$. Furthermore, dose dumping and inter-intra subject variation is minimized. Additionally, there is no need for a solubilizer in the raltegravir formulation when the non-gelling polymer is used.

The table below provides the results of a comparative dissolution profile of a raltegravir potassium tablet formulation prepared with a non-gelling polymer and a comparative raltegravir potassium tablet formulation prepared without a nongelling polymer. The dissolution conditions: 0.001N HCl, 900 ml, USP-II, 100 rpm. As can be seen, the formulation containing non-gelling polymer releases less raltegravir active at the low pH conditions used in the study. The delay will help prevent undue precipitation and degradation of the active. In comparison, the formulation without the non-gelling polymer exhibits a decrease in concentration of the active over time due to the active getting degraded.

| | % Cumulative Drug Release | |
|---|---|---|
| Time in Minutes | Without Non-gelling Polymer | With Non-gelling Polymer |
| 15 | 59 | 41 |
| 30 | 76 | 60 |
| 45 | 71 | 75 |
| 60 | 48 | 82 |
| 90 | 31 | 85 |

We claim:

1. A solid pharmaceutical composition, comprising:
raltegravir or a pharmaceutically acceptable salt thereof,
0.5 to 5 wt % of a polyethylene oxide based on the total weight of the composition, and one or more pharmaceutically acceptable excipients,
wherein the polyethylene oxide is the only non-gelling polymer in the formulation.

2. The solid pharmaceutical composition of claim 1, wherein the composition is free of a solubilizing agent.

3. The solid pharmaceutical composition of claim 1, wherein the composition is in the form of a tablet, capsule, Multiple Unit Pellet System, granules, pellets, beads, particles, or mini-tablets.

4. The solid pharmaceutical composition of claim 1, wherein the composition is in the form of a tablet.

5. The composition of claim 1, wherein the raltegravir is in the form of amorphous raltegravir potassium, raltegravir potassium crystalline Form H1, crystalline raltegravir potassium monohydrate, crystalline raltegravir potassium dihydrate or a combination thereof.

6. The solid pharmaceutical formulation of claim 1, wherein the raltegravir is raltegravir potassium in amorphous form.

7. A solid pharmaceutical tablet, consisting of:
raltegravir or a pharmaceutically acceptable salt thereof,
a polyethylene oxide in an amount of 0.5 to 5 wt %,
one or more pharmaceutically acceptable excipients selected from diluents, binders, lubricants and glidants, and
optionally a film coating,
wherein the polyethylene oxide is the only non-gelling polymer in the formulation.

8. The solid pharmaceutical tablet of claim 7, wherein the raltegravir is raltegravir potassium in amorphous form.

9. The solid pharmaceutical tablet of claim 7, wherein the one or more pharmaceutically acceptable excipients include microcrystalline cellulose, lactose, magnesium stearate and sodium stearyl fumarate.

10. The solid pharmaceutical composition of claim 1, wherein the composition is free of an anti-nucleating agent selected from hydroxyalkylcellulose, alkylcellulose, polyvinylpyrrolidone and polyacrylic acid.

11. The solid pharmaceutical tablet of claim 7, wherein the composition is free of an anti-nucleating agent.

12. The solid pharmaceutical composition of claim 1, wherein the amount of polyethylene oxide is 1 to 5 wt % based on the total weight of the composition.

13. The solid pharmaceutical composition of claim 1, wherein the amount of polyethylene oxide is 2 to 5 wt % based on the total weight of the composition.

* * * * *